United States Patent [19]

Greene et al.

[11] E Patent Number: Re. 32,833

[45] Reissued Date of Patent: Jan. 17, 1989

[54] SCREENING VACCINES AND IMMUNIZATION PROCESS

[75] Inventors: Mark I. Greene, Penn Valley, Pa.; Bernard N. Fields, West Newton, Mass.

[73] Assignee: President and Fellows of Harvard College, Cambridge, Mass.

[21] Appl. No.: 4,172

[22] Filed: Dec. 23, 1986

Related U.S. Patent Documents

Reissue of:

[64] Patent No.: 4,490,358
Issued: Dec. 25, 1984
Appl. No.: 353,257
Filed: Mar. 1, 1982

[51] Int. Cl.[4] ..... A61K 39/395; A61K 39/42; G01N 33/54; G01N 33/56

[52] U.S. Cl. ..... 424/86; 424/85.8; 424/87; 436/548

[58] Field of Search ..... 424/85, 86, 88, 89; 435/172.2; 436/548

[56] References Cited

PUBLICATIONS

Nisonoff et al., Clinical Immunology and Immunopathology, vol. 21, pp. 397–406, (1981).

Moshly-Rosen et al., FEBS Letters, vol. 106, pp. 389–392, (1979).

Letvin et al., The J. of Immunology, vol. 127, pp. 2334–2339, (1981).

Nepom et al., J. Exp. Med., vol. 155, pp. 155–167, (1982).

*Primary Examiner*—Blondel Hazel

[57] ABSTRACT

Mammals are vaccinated against infectious organisms and polypeptides are screened for utility as vaccines by a complementing set of monoclonal antibodies, the first of which antibodies binds specifically to the site on the organism which itself binds specifically to a receptor on a host cell of the mammal, and the second of which binds specifically to the first. Vaccination is done with the second antibody alone, and screening is done by determining whether the polypeptide binds to the first antibody.

12 Claims, 2 Drawing Sheets

OPERATING SYSTEM

Figure 2:
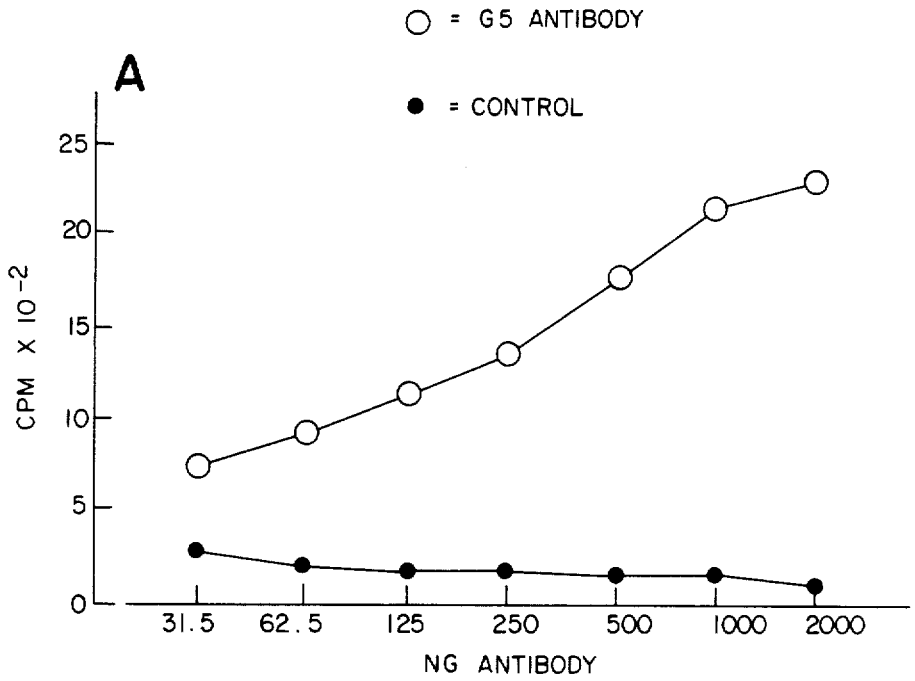
Figure 2:
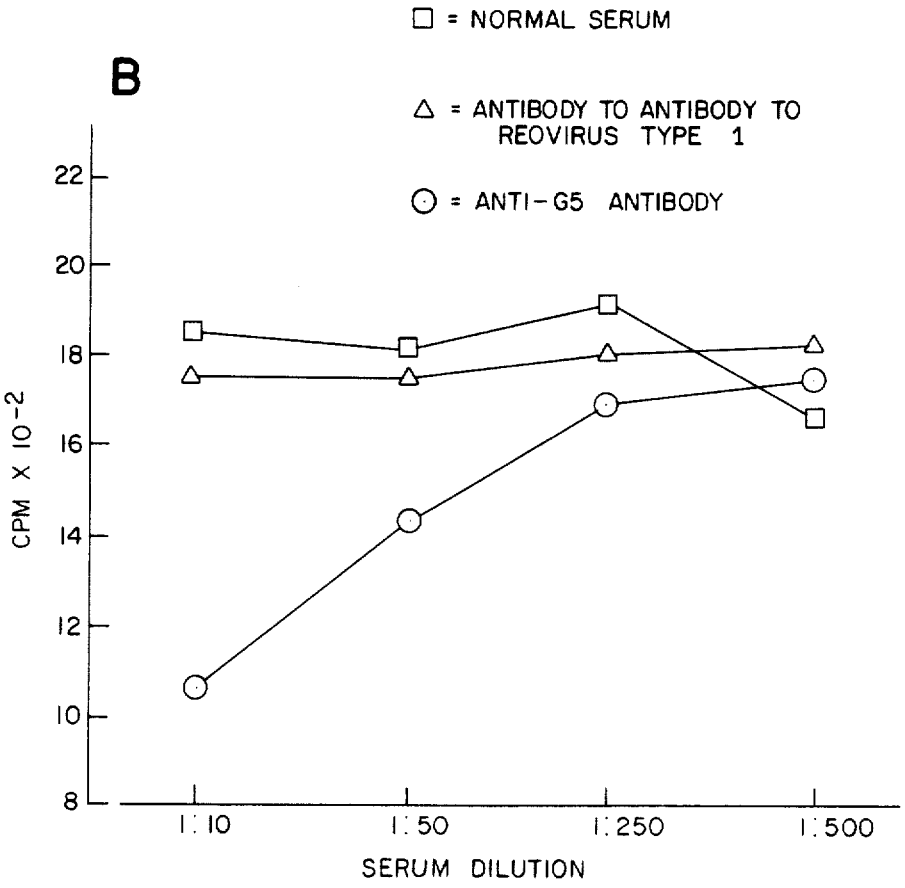

OPERATION OF $MC_1 - MC_2$
DISRUPTED BY POLYPEPTIDES

SCREENING VACCINES AND IMMUNIZATION PROCESS

Matter enclosed in heavy brackets [ ] appears in the original patent but forms no part of this reissue specification; matter printed in italics indicates the additions made by reissue.

The invention described herein was made in the course of work under a grant from the Department of Health and Human Services.

This invention relates to immunization of mammals against infectious organisms having sites binding specifically to host cells of the mammals by inoculating the mammals with a second successive monoclonal antibody against such sites and also relates to a method of screening polypeptides for potential vaccine activity against such infectious organisms by determining whether they bind to the first monoclonal antibody to the organism at the site which binds specifically to a receptor site on a host cell.

Infectious organisms such as bacteria, funguses, parasites, viruses and the like function by binding specifically to mammalian host cells, each organism having a site which binds specifically to a complementary portion, called a receptor site, of the host cells. It has now been found that by providing a monoclonal antibody specific to the binding site of the organism, then providing a second monoclonal antibody specific for the combining site of the first, the second antibody can be used as a surrogate for the infectious organism in providing immunization of a host mammal by inoculation. In this case, in which a host mammal is inoculated with the second monoclonal antibody, a decrease in infectivity of the mammal by the organism is brought about without any contact of the mammal with the infectious organism itself. This procedure is of particular importance in the case of a dangerous infectious organism such as the rabies virus. In the screening polypeptides for potential vaccine activity, whether the polypeptide be a synthetic polypeptide or an infectious organism of attenuated virulence, only those polypeptides which bind specifically to the first monoclonal antibody are capable of functioning as vaccines against the original infectious organism.

While the methods of the present invention can be employed with any infectious organisms such as bacteria, fungi, parasites, viruses or the like, they are particularly applicable to viruses, including reoviruses and rotaviruses as well as those viruses against which it has been particularly difficult in the past to provide effective nonvirulent vaccines, such as respiratory syncitial virus, and dangerous viruses such as rabies.

The present invention provides a method of immunizing a host mammal against an infectious organism having a site which binds specifically to a receptor site on a host cell, which method comprises providing a first monoclonal antibody which binds specifically to said organism site, providing a second monoclonal antibody which binds specifically to the first, and inoculating the mammal with an effective amount of said second antibody to bind specifically to said receptor site and block binding of said organism thereto. The present invention also provides a method of screening polypeptides for potential vaccine activity against an infectious organism having a site which binds specifically to a receptor site on a host cell, which method comprises providing a first monoclonal antibody binding specifically to said organism site, and determining whether said polypeptide binds specifically to said first antibody. The extent of such polypeptide binding can be measured by conventional immunoassay procedures. Extent of binding can be determined directly by labelling either the unknown polypeptide or the first monoclonal antibody of the pair and immobilizing the other of the pair of adsorbing on a solid surface of synthetic plastic. Extent of binding can also be determined indirectly by immobilizing one member of the pair, for example the first monoclonal antibody, and allowing the other, for example the unknown, to compete with a known quantity of labelled second antibody (whether monoclonal or not) or of labelled infectious organism in binding to the immobilized first monoclonal antibody. In an alternative example the second antibody (whether monoclonal or not) is immobilized and the unknown polypeptide is allowed to compete with a known quantity of labelled first monoclonal antibody in binding to the second immobilized antibody.

Figure 1:
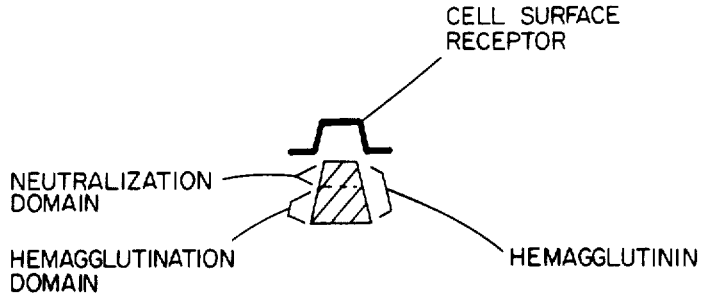
Figure 1:
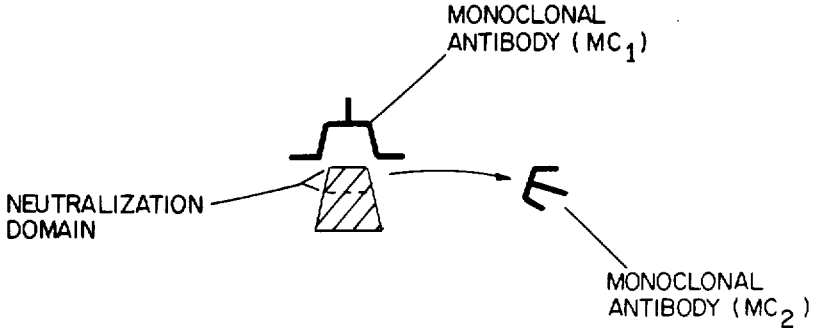
Figure 1:
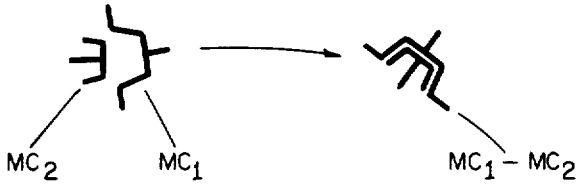
Figure 1:
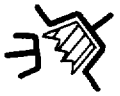

In the drawings,

FIG. 1 is a schematic showing symbolically the preparation of the two monoclonal antibodies and their use for screening polypeptides, and FIG. 2 is a graphical summary of radioimmunoassays showing measurement of the extent of binding of the first monoclonal antibody to viral hemagglutinin and to other polypeptides.

As represented in FIG. 1, the infectious organism, the binding site of a virus, depicted as the viral hemagglutinin, binds specifically to a host cell surface receptor, while the first monoclonal antibody ($MC_1$) also binds specifically to the same site of the viral hemagglutinin to neutralize it. The second monoclonal antibody ($MC_2$) binds specifically to the same binding site of $MC_1$ as does the neutralization domain of the viral hemagglutinin. Since any polypeptide to be used as a vaccine must bind specifically to the host cell surface receptor, and since polypeptides which are incapable of bonding to $MC_1$ are incapable of specific binding to the cell surface receptor, determining extent of binding of polypeptides to $MC_1$ is useful for screening polypeptides as potential vaccines.

The monoclonal antibodies employed in the present invention are made by conventional procedures. An animal such as a mouse is first injected with the infectious organism, its spleen cells are removed and fused with myeloma cells to form hybridoma cells, the latter are cloned in a serum-containing medium, and the monoclonal antibodies produced are separated from the medium. The monoclonal antibodies are then screened by neutralization assay to select those antibodies which bind to the site on the infected organism which binds specifically to the receptor site on the cells of the host, as measured by determining the decrease in infectivity of the organism after treatment with the antibody.

The neutralizing monoclonal antibodies are then injected into other animals such as mice, the spleen cells are removed and fused with myeloma cells to produce second hybridoma cells which are then cloned in a serum-containing medium to produce second monoclonal antibodies. The second monoclonal antibodies thus produced bind specifically to the same receptor sites on the host cells as do the original infectious organisms.

The second monoclonal antibodies thus produced can be injected into mammals in an amount effective to bind specifically to the receptor sites on the host cells and block binding of the infectious organism thereto, thus decreasing the infectivity of the organism without any contact between the organism and the host.

The first monoclonal antibody can also be used to screen unknown or test polypeptides (either synthetic polypeptides or live infectious organisms of attenuated virulence) for potential utility as vaccines, only those polypeptides which bind specifically to the first monoclonal antibody being capable of acting as vaccines.

Any conventional immunoassay procedure can be used to determine the extent to which the unknown polypeptides bind specifically to the first monoclonal antibody. Among suitable procedures are the following in which radioactive labelling is used:

1. Immobilize the first monoclonal antibody by adsorbing it on the surface of a synthetic plastic test tube or well, and incubate in contact with it an aqueous medium containing both the unknown polypeptide and a quantity of the labelled infectious organism, washing, and subjecting the tube to counting. A low count means that the polypeptide may be an effective vaccine.
2. Immobilizing the first monoclonal antibody, then incubating it with both the unknown polypeptide and a labelled quantity of a second antibody (whether monoclonal or not) specific to the first monoclonal antibody, washing, and counting. A low count means that the polypeptide may be an effective vaccine.
3. Immobilizing the first monoclonal antibody, then incubating it with a quantity of labelled unknown polypeptide, washing, and counting. A low count means that the unknown is ineffective as a vaccine.
4. Immobilizing the second antibody (whether monoclonal or not), incubating with both the unknown polypeptide and a labelled quantity of first monoclonal antibody, washing, and counting. A low count means that the polypeptide may be effective as a vaccine.
5. Immobilizing the infectious organism, incubating with both the unknown polypeptide and labelled first monoclonal antibody, washing, and counting. A low count means that the unknown may be effective.
6. Immobilizing the unknown polypeptide, incubating with both the infectious organism and labelled first monoclonal antibody, washing, and counting. A low count in this case means that the unknown is ineffective as a vaccine.

In each of the foregoing assay procedures a standard or control specimen known to be effective or known to be ineffective as a vaccine may be used for purpose of comparison.

Two of the foregoing assay procedures are particularly preferred, the second and the fourth, because each can be carried out without the need for coming into contact with an infectious organism and without the need for any special treatment of the unknown polypeptide such as labelling or immobilizing it. The fifth procedure can be used when the infectious organism can be obtained in a pure form; it is desirable only if the organism is not dangerous for laboratory use.

Enzyme or fluorescent labels can be used instead of radioactive labels, as is well known. In addition, when infectious organism is used in the assay, as for example in the first procedure described above, there may be used only a fraction of the organism containing a binding site which binds specifically to a receptor site on the host cells (such as $I^{125}$ labelled viral hemagglutinin).

This screening procedure, as pointed out above, can also be effectively carried out using in place of the second monoclonal antibody any ordinary antibody such as rabbit antibody grown by injecting rabbits with the first monoclonal antibody and harvesting in the usual manner. However, best results are obtained using monoclonal antibody as the second antibody.

The screening procedure, by eliminating many potential vaccines without the need for testing by inoculation of host mammals, greatly facilitates development of vaccines.

The following examples will serve to illustrate more fully the nature of the present invention without acting as a limitation upon its scope.

EXAMPLE

Immunization of mice

Adult mice were immunized with mammalian reovirus type 3 (Dearing), an infectious organism which results in a highly fatal encephalitis in suckling mice. BALB/c mice were obtained from the National Institutes of Health. The mice did not have neutralizing antibody against reovirus at the time of the initial immunization. The mice were immunized by intraperitoneal injection of $5\times10^7$ PFU of gradient purified type 3 reovirus (Dearing) in gelatin-saline (0.8% NaCl, 0.003% $CaCl_2$, 0.07% $MgCl_2$, $6H_2O$, 0.12% $H_3BO_3$, 0.005% $Na_2B_4O_7$, $10H_2O$, 0.3% gelatin). Injection occurred initially four months and again one month prior to the myeloma cells fusions. Three days prior to the fusion, the animals were inoculated intravenously with $3\times10^7$ PFU of virus in gelatin-saline. The spleens of three immunized animals were aseptically removed and the spleen cells were dispersed by repeated flushing with Dulbecco's modified minimal essential medium (DMEM) at 4°.

Myeloma Cells

The mouse myeloma cell line BALB/c P-3-NS1/1-Ag4-1 (NS1) (Kohler and Milstein, 1976) was maintained in suspension culture in DMEM supplemented with 7.5% heat inactivated (56°, 30 min.) fetal calf serum (FCS) and 7.5% heat inactivated agamma newborn calf serum (DMEM)-15%).

Construction of Hybridomas

The spleen cells were washed with DMEM and mixed with MS1 myeloma cells at a ratio of 4:1. The cells were pelleted by centrifugation and fused with 50% polyethylene glycol (PEG 1500) (Nowinski et al., 1979, Lostrom et al., 1979). After fusion, the cells were pelleted and resuspended in DMEM containing 20% fetal calf serum (DMEM-20%) and were dispersed into 96 well microtiter plates (Linbro). On day one, a half volume of DMEM-20% containing $10^{-4}$ M hypoxanthine, $4\times10^{-7}$ M aminopterin, $1.6\times10^{-5}$ M thymidine and $3\times10^{-6}$ M glycine (HAT media) was added. On day 2, 3, 6, 9, 12 and 15 half the media was removed and replaced with HAT media. After day 15, media was replaced with DMEM-20% containing $10^{-4}$ M hypoxanthine and $1.6\times10^{-5}$ M thymidine (Nowinski et al., 1979). Colonies became visible between the second and third week after initiation of the culture. Culture supernatants were screened for anti-viral antibodies by a radioimmunoassay procedure. The reovirus was added to polyvinyl chloride plates (Cooke Engineering Co.) at $10^9$ pfu/well in 25 μl PBS and allowed to air dry. The plates were then incubated with 50 μl of methanol per well until dry; and then with 5% bovine serum albumin (BSA) for 2-3 hours. Culture fluids (25 μl) from the hybridoma cells were added to each well and kept at 37° for one hour. The wells were then washed 4 times with PBS-1% BSA (Lostrom et al., 1979). Rabbit antimouse IgG antisera (Cappel) that had been iodinated with chloramine T (Greenwood et al., 1963) was added ($10^5$ cpm/well) and the plates were incubated overnight at 4°. The specific activity of the iodinated antiserum was $1.8\times10^6$ cpm/mg of protein. Wells were washed five times with PBS, cut out, and counted in a gamma counter.

Hybridoma Cell Cloning

Hybrid cell lines producing monoclonal antibodies, as determined by the foregong radioimmunoassay, were cloned by dilution and growth in 0.3% agar (Cotton et al., 1973). Colonies were allowed to grow until readily visible by eye. They were then transferred with a pasteur pipette to one well of a 96-well plate containing 0.1 ml of IMEMZO (improved minimal essential media supplemented with zinc, insulin, and Hepes buffer) media (International Biological Laboratories, Inc.) containing 15% FCS. Cells were grown up to mass culture and subsequently maintained in IMEMZO containing 5% heat inactivated fetal calf serum and 5% agamma newborn calf serum.

Isolation of First Monoclonal IgG Antibody

Cloned hybridoma cell cultures, grown up to a 400 ml volume by daily feedings with fresh media were maintained at this volume for 48 hours and the cells were removed by centrifugation at 400 g for 20 min. The supernatants were removed and phenylmethylsulfonyl fluoride (PMSF) was added to a concentration of 100 μg/ml. The supernatant was applied to a 3 ml bed volume column of protein A-Sepharose CL-4B (Sigma) at a flow rate of approximately 25 ml/hr (Lee et al., 1981). The column was washed with PBS until no protein was detectable in the eluent and the IgG was eluted with 0.1M glycine-HCl (pH 2.5). The fractions containing IgG were pooled (4 ml) and dialyzed against PBS (4 liters). Aliquots were stored at −20°. All antibodies were used at a concentration of 1-2 mg/ml.

Neutralization Assays

Virus preparation were diluted to $2\times10^3$ PFU/ml in gelatin-saline. Purified and isolated hybridoma IgGs prepared as described were diluted serially in 5-fold steps in gelatin-saline and 0.2 ml of the IgG dilutions was mixed with 0.2 ml of the virus. The neutralization was carried out at 34° for 1 hr (Weiner and Fields, 1977). Duplicate 0.1 ml samples were then plated in 6 well cluster dishes (Costar) and allowed to adsorb for 1 hr. The cells were then overlaid with agar and the plaque assays were performed as reported previously (Fields and Joklik, 1969). The neutralization titer is expressed as the higest dilution of antibody which neutralized 80% of the input virus (Weiner and Fields, 1977).

The desired first monoclonal antibody, designated as G5, exhibited no detectable neutralization of reoviruses of serotype 1 (Lang) or 2 (Jones) at a 1:10 dilution of antibody, but exhibited effective neutralization titer of 12,500 against the reovirus serotype 3 (Dearing) which had been used to immunize the mice, as well as neutralization of additional type 3 isolates from natural sources (Hrdy et al., 1979). The antibody subclass was determined by ouchterlony analysis to be $IgG_{2a}$. It was determined to be specific to the viral σ-1 protein, a viral outer capsid protein of serotype 3 by immunoprecipitation of $^{35}$S-methionine labelled infected cell lysates, and thus was specific to the site which has been well known to be involved in binding the virus to host cell receptors.

Isolation of Second Monoclonal IgG Antibody

The development and screening of the second monoclonal antibody involved the immunization of BALB/c mice with purified G5 monoclonal antibodies in complete Freund's adjuvant. 100 μg of $G_5$ monoclonal antibody was used to prime and then boost three weeks later the same mouse. Five days later the spleen was removed and splenocytes subjected to fusion using the same procedure as described above for construction of hybridomas except that another generally available mouse myeloma cell line (653) was used in place of NS1. Culture conditions were the same. Positive wells were determined by their ability to secrete antibody which would selectively bind the G5 monoclonal antibody fixed to a polyvinyl chloride plate as described above. Controls used included 653 supernatant and irrelevant monoclonals of the same isotype and allotype. Positive clones were those which were found to selectively bind G5; They were then shown to bind to the hemagglutinin binding site of reovirus on a variety of somatic cell lines including the R1.1 (H-$2^k$) thymoma line, the R1.E (H-$2^k$ thymoma line), human T cells but not YAC (H-$2^a$) lymphoma cells. All of these lines bind or do not bind the hemagglutinin (HA) in the same manner as the second monoclonal antibody. In this manner a G5 binding monoclonal antibody (anti-G5 antibody) was selected which could selectively bind to sites on cells which were themselves structured to bind specifically the HA of reovirus.

Competition of Second Monoclonal Antibody With Virus in Infectivity

The anti-G5 antibody was then evaluated to examine its ability to compete for virus in an infectivity assay. BW 5147 AKR lymphoma cells were plated in linbro wells at a density of $2\times10^6$ cells/well. The BW 5147 cell expresses the receptor for the neutralization domain of the HA. Consequently the BW 5147 cell will bind to reovirus and become infected with reovirus. The BW 5147 cell also binds the anti-G5 monoclonal antibody. Incubating $1\times10^7$ plaque forming units (pfu) of reovirus with the BW 5147 cells led to large numbers $>10^7$ pfu infections virus recoverable from 100% of these cells several days later. Incubation of the virus, the BW 5147 cells and the monoclonal anti-G5 antibody (100 μ 1 of ascites) resulted in 0% of infected cells. Thus protection is absolute for local infections in tissue culture.

Use of Second Monoclonal Antibody As Immunization Agents

Hybridoma cells bearing the Anti-G5 antibody prepared as described above were used to prime naive BALB/c mice. The spleens of these mice were evaluated for cyto-toxic activity against reovirus infected targets after in vitro restimulation for 5 days at 37° C. with reovirus infected stimulator cells. The cells were cultured in 2 ml of RPMI 1640 medium (M.A. Bioproducts, Walkersville, Md.) supplemented with 5% fetal calf serum, 100 $\mu$/ml penicillin, 100 $\mu$g/ml streptomycin and $5\times10^{-5}$ M 2-mercaptoethanol in 16 mm wells (Linbro Scientific, Hamden, Conn.) in a 5% $CO_2$ humidified air atmosphere. Cell density was $10^6$ responders/$10^5$ stimulators. In vitro stimulation of spleen cells with infected stimulators but without in vivo priming does not produce cytotoxic activity ($\lesssim$5%). Anti-G5 primed mice developed significant ($\gtrsim$30%) cytotoxicity at an effector target ratio of 100:1, when assayed on reovirus infected target cells. The targets were reovirus infected L cells and a standard $Cr^{51}$ release assay was used. Thus the anti-G5 antibody is completely protective for local infection and can readily prime for reovirus specific CTL.

Screening of Polypeptides

In providing a screening for determining potential vaccine activity of polypeptides, it was first demonstrated that the first monoclonal antibody (G5 ) could be immobilized while retaining its ability to bind specifically to infectious organism, i.e., to the hemaglutinin portion (HA) of reovirus type 3, the hemagglutinin containing the binding site which is capable of binding specifically to the receptor on the host cell. There was used purified HA isolated from reovirus type 3 infected cell lysates. The HA was affinity-purified by passage through Sepharose 4B beads to which G5 was coupled. The HA was selectively eluted from the beads by acid, pH 2.8 glycine HCl. A radioimmunoassay was developed in which the binding of G5 antibody to radiolabelled HA was measured. Purified hemagglutinin protein (HA) from reovirus type 3 was radiolabelled with $I^{125}$ by the chloramine-T method to a specific activity of 3000 cpm/ng. As a control antibody, there was used a monoclonal antibody 4S produced from an anti-Sendai virus B cell hybridoma which secretes an anti-Sendai antibody of the same isotype as anti-G5 (IgM). Monoclonal antibody G5 or control monoclonal antibody 4S were partially purified from culture supernatants from hybridoma cell lines and adsorbed onto the bottom of polyvinyl microtitre plates (Cooke, Dynatech) as previously described. After incubation with phosphate buffered saline (PBS) containing 10 mg/ml of bovine serum albumin (BSA) to saturate unbound sites on the plastic adsorbent, 10 ng of radiolabelled HA in 20 $\mu$l PBS were then added to each well for 60 minutes incubation at room temperature. Following extensive washing and drying, well bottoms were removed and counted in a Beckman 4000 gamma counter; determinations represent triplicate means$\pm$standard error. The results are shown in FIG. 2A of the drawing.

The extent of binding of several different polypeptides to G5 was measured by immobilizing the G5 , then incubating it with both a polypeptide and with labelled HA. The G5 was immobilized by adsorbing 250 ng of G5 onto the bottom of each well of a microtitre plate and incubating with BSA as described above. Test antisera, either normal sera, antibodies to antibodies to reovirus type 1 (anti-anti-R1), or antibodies to mouse antibodies to reovirus type 3 (anti-G5 ), were then incubated in the wells for 60 minutes at room temperature. After extensive washing, 10 ng of radiolabelled HA in 20 $\mu$l PBS was added and the assay performed as before, with the results shown in FIG. 2B. As is seen, only the potential vaccine anti-G5 bound to the G5 , as shown by the decreased count, whereas the other polypeptides, normal sera and the anti-anti-R1 did not. Stated another way, the decrease in the count for anti-G5 antibody measures the extent to which the binding of G5 to anti-G5 is disrupted by competition of the labelled HA with the anti-G5 . Conversely, the HA can be immobilized by adsorption, incubated with the test serum and with labelled G5 antibody; again, a decrease in count indicates that the test serum is a potential vaccine.

By substituting other polypeptides, such as attenuated virus or synthetic polypeptides, for the normal sera or anti-anti-R1 in the foregoing assay, their potential effectiveness as vaccines against reovirus type 3 can be measured.

What is claimed is:

1. The method of immunizing a host mammal against an infectious organism having a site which binds specifically to a receptor site on a host cell which method comprises providing a first monoclonal antibody which binds specifically to said organism site, providing a second monoclonal antibody which binds specifically to the first, and inoculating said mammal with an effective amount of said second antibody to [bind specifically to said receptor site and block binding of said organism thereto.] *immunize said mammal.*

2. The method as claimed in claim 1 in which the infectious organism is a virus.

3. The method of screening polypeptides for potential vaccine activity against an infectious organism having a site which binds specifically to a receptor site on a host cell, which method comprises providing a first monoclonal antibody binding specifically to said organism site, and determining whether said polypeptide binds to said antibody.

4. The method as claimed in claim 3 in which said organism is a virus.

5. The method as claimed in claims 3 or 4 in which the binding is determined by measuring competitive binding of said polypeptide and of a labelled specimen of said organism to said antibody.

6. The method of claim 4 in which the binding is determined by measuring competitive binding to said antibody of said polypeptide and of radiolabelled viral hemagglutinin containing a site which binds specifically to a receptor site on a host cell.

7. The method of screening polypeptides for potential vaccine activity against an infectious organism having a site which binds specifically to a receptor site on a host cell, which method comprises providing a first monoclonal antibody binding specifically to said organism site, providing a second antibody binding specifically to the first, and determining whether said polypeptide interferes with the binding of said second antibody to said first antibody.

8. The method as claimed in claim 7 in which said organism is a virus.

*9. The method as claimed in claim 1 in which said second antibody binds specifically to said receptor site and blocks binding of said organism thereto.*

*10. The method as claimed in claim 9 in which the infectious organism is a virus.*

*11. The method of immunizing a host mammal against an infectious organism having a site which binds specifically to a receptor site on a host cell which method comprises*

*providing a first monoclonal antibody which binds specifically to said organism site,*

*providing a second monoclonal antibody which binds specifically to the first, and*

*inoculating said mammal with an effective amount of said second antibody to serve as a surrogate antigen for the infectious organism in providing immunization of the host mammal.*

*12. The method of immunizing a host mammal against an infectious organism having a site which binds specifically to a receptor site on a host cell which method comprises*

*providing a first monoclonal antibody which binds specifically to said organism site,*

*providing a second monoclonal antibody which binds specifically to the first, and*

*inoculating said mammal with an effective amount of said second antibody to block the binding of the infectious organism to said receptor site.*

* * * * *